(12) United States Patent
Mitzlaff et al.

(10) Patent No.: US 8,936,595 B2
(45) Date of Patent: Jan. 20, 2015

(54) SURGICAL INSTRUMENT, PARTICULARLY ELECTROSURGICAL INSTRUMENT

(76) Inventors: Lothar Mitzlaff, Lagos (PT); Ralf Krause, Hildrizhausen (DE)

( * ) Notice: Subject to any disclaimer, the term of this patent is extended or adjusted under 35 U.S.C. 154(b) by 942 days.

(21) Appl. No.: 13/078,625

(22) Filed: Apr. 1, 2011

(65) Prior Publication Data

US 2011/0245825 A1 Oct. 6, 2011

(30) Foreign Application Priority Data

Apr. 1, 2010 (DE) .......................... 10 2010 016 291

(51) Int. Cl.
*A61B 18/14* (2006.01)
*A61B 17/00* (2006.01)
*A61B 17/29* (2006.01)
*A61B 18/00* (2006.01)

(52) U.S. Cl.
CPC ... *A61B 18/1442* (2013.01); *A61B 2017/00353* (2013.01); *A61B 2017/2922* (2013.01); *A61B 2017/2923* (2013.01); *A61B 2018/00916* (2013.01); *A61B 2018/1412* (2013.01); *A61B 2018/1455* (2013.01)
USPC .................. 606/51; 606/52; 606/205; 606/46

(58) Field of Classification Search
USPC ...................... 606/20–52, 205–207
See application file for complete search history.

(56) References Cited

U.S. PATENT DOCUMENTS

| | | | |
|---|---|---|---|
| 5,190,541 A * | 3/1993 | Abele et al. ...................... | 606/46 |
| 5,190,560 A * | 3/1993 | Woods et al. ................. | 606/137 |
| 5,562,655 A | 10/1996 | Mittelstadt et al. | |
| 5,735,848 A * | 4/1998 | Yates et al. ...................... | 606/48 |
| 5,766,169 A * | 6/1998 | Fritzsch et al. .................. | 606/48 |
| 5,772,660 A * | 6/1998 | Young et al. .................... | 606/42 |
| 6,193,718 B1 * | 2/2001 | Kortenbach et al. ............ | 606/50 |
| 6,402,748 B1 * | 6/2002 | Schoenman et al. ............ | 606/45 |
| 6,409,728 B1 * | 6/2002 | Ehr et al. ......................... | 606/51 |
| 6,447,511 B1 * | 9/2002 | Slater ............................... | 606/48 |
| 6,458,129 B2 * | 10/2002 | Scarfi .............................. | 606/50 |
| 6,616,658 B2 * | 9/2003 | Ineson ............................. | 606/42 |
| 6,673,087 B1 * | 1/2004 | Chang et al. .................. | 606/174 |
| 6,702,813 B1 * | 3/2004 | Baxter et al. .................... | 606/49 |
| 7,083,617 B2 * | 8/2006 | Kortenbach et al. ............ | 606/46 |

(Continued)

FOREIGN PATENT DOCUMENTS

| | | |
|---|---|---|
| DE | 100 84 618 B4 | 8/2009 |
| EP | 0 875 209 A1 | 11/1998 |

(Continued)

*Primary Examiner* — Michael Peffley
(74) *Attorney, Agent, or Firm* — Dickstein Shapiro LLP (57) ABSTRACT

A surgical instrument, particularly an electrosurgical instrument, including an actuating element for actuating at least one first and one second functional unit, wherein the actuating element is movable in a translational and/or rotational motion within a movement range, wherein the first functional unit is actuatable by means of a movement within a first partial region of the movement range and the second functional unit is actuatable by means of a movement within a second partial region of the movement range, wherein a changeover device is provided such that, as a result of a movement of the actuating element through a changeover region between the first and second partial region, an operative connection between the first functional unit and the actuating element can be interrupted and an operative connection can be established between the second functional unit and the actuating element.

25 Claims, 10 Drawing Sheets

(56) References Cited

U.S. PATENT DOCUMENTS

| | | | |
|---|---|---|---|
| 7,131,970 B2 * | 11/2006 | Moses et al. | 606/51 |
| 7,255,697 B2 * | 8/2007 | Dycus et al. | 606/49 |
| 7,367,976 B2 * | 5/2008 | Lawes et al. | 606/51 |
| 7,628,791 B2 * | 12/2009 | Garrison et al. | 606/51 |
| 2003/0109872 A1 * | 6/2003 | Muzzammel | 606/45 |
| 2005/0096645 A1 * | 5/2005 | Wellman et al. | 606/41 |
| 2005/0149017 A1 * | 7/2005 | Dycus | 606/51 |
| 2005/0256533 A1 * | 11/2005 | Roth et al. | 606/167 |
| 2006/0074415 A1 * | 4/2006 | Scott et al. | 606/45 |
| 2006/0217706 A1 * | 9/2006 | Lau et al. | 606/45 |
| 2006/0271042 A1 * | 11/2006 | Latterell et al. | 606/51 |
| 2007/0078456 A1 * | 4/2007 | Dumbauld et al. | 606/42 |
| 2007/0135803 A1 * | 6/2007 | Belson | 606/1 |
| 2007/0173814 A1 * | 7/2007 | Hixson et al. | 606/51 |
| 2007/0185487 A1 * | 8/2007 | Hafner | 606/45 |
| 2007/0213708 A1 * | 9/2007 | Dumbauld et al. | 606/45 |
| 2007/0260242 A1 * | 11/2007 | Dycus et al. | 606/51 |
| 2008/0009854 A1 * | 1/2008 | Yates | 606/42 |
| 2008/0033423 A1 * | 2/2008 | Peacock, III | 606/34 |
| 2008/0167644 A1 * | 7/2008 | Shelton et al. | 606/34 |
| 2008/0167670 A1 * | 7/2008 | Shelton et al. | 606/167 |
| 2008/0319442 A1 * | 12/2008 | Unger et al. | 606/48 |
| 2009/0131932 A1 * | 5/2009 | Vakharia et al. | 606/48 |

FOREIGN PATENT DOCUMENTS

| | | |
|---|---|---|
| EP | 1 621 142 A2 | 2/2006 |
| WO | WO 01/66025 A1 | 9/2001 |

* cited by examiner

SURGICAL INSTRUMENT, PARTICULARLY ELECTROSURGICAL INSTRUMENT

FIELD OF THE INVENTION

The disclosed embodiments relate to a surgical instrument, particularly an electrosurgical instrument.

BACKGROUND

Surgical instruments which have a plurality of functions are known in the art. In combined instruments of this type, there is no need for a changeover between the "individual instruments" needed at any particular time. For example, laparoscopic operations in which a change of instruments usually involves a complex removal from, and introduction into, the trocar, can thus be carried out more efficiently. Combined instruments, for example, for sealing vessels and for cutting tissue are known.

A common use of such instruments is the excision of tissue. During excision, in a first step, tissue is grasped and coagulated. In a second step, the coagulated section is parted with a cutting instrument. The coagulation is carried out to close blood vessels and prevent bleeding during cutting. These steps are repeated as often as needed until the tissue bundle is removed from the body. Procedures of this type are standard for cancerous conditions, for example, in the case of a hysterectomy, wherein the uterus is removed.

An instrument of this type requires a first functional unit for grasping the tissue and a second functional unit for cutting the tissue, wherein a mechanism for transmitting force or movement must be provided. The relevant force can be applied by the user by means of operating elements, for example, a hand trigger or a finger trigger, on a handle.

Surgical instruments belonging to the prior art conventionally have a plurality of actuating elements, wherein each actuating element is assigned to a functional unit. In this way, functional units can be operated separately. For example, a hand trigger for grasping, a finger trigger for cutting, and a separate coagulation switch can be provided. Separate construction of the actuating elements is perceived to be disadvantageous, causing repeated interruptions in the operation because, for example, smooth grasping and cutting in one movement is not possible. The user is also restricted, for example, if the index finger is used for cutting and is no longer available for activating the coagulation process. The various actuating elements also lead to increased costs and comparatively bulky instruments. As a result, it becomes increasingly difficult to maintain oversight of such an instrument during use.

Surgical instruments in which two different functions, specifically grasping and cutting tissue, can be controlled with just one actuating element are also known in the prior art. For example, U.S. Pat. No. 7,628,791 describes an electrosurgical instrument for coagulating and cutting tissue. Three different functions, specifically grasping, coagulating, and cutting the tissue, are controlled with just one actuating element. If the hand trigger provided is moved through a first travel segment, the jaw part closes and, if said trigger is moved farther, a coagulation switch is actuated. If said trigger is moved yet farther, a blade is guided through the clamped tissue. A force must be exerted by the user over the whole range of movement in order to hold the tissue firmly, wherein the counterforce of a spring is overcome. For arresting a grasping position, locking devices are proposed in U.S. Pat. No. 7,628,791, although said locking devices permit only locking before the cutting process takes place. During the cutting process, corresponding locking is not possible and would also be disadvantageous because, in the known device, the cutting knife could not be moved back again. Therefore, the user is restricted when using the instrument described in U.S. Pat. No. 7,628,791 because, for example, during cutting of the tissue, it must be ensured that the tissue is sufficiently well-grasped.

SUMMARY

It is an object of the disclosed embodiments to provide a surgical instrument including at least two functional units which provide easy and reliable operation.

This aim is achieved with a surgical instrument, particularly an electrosurgical instrument.

Disclosed embodiments include an electrosurgical instrument, including an actuating element for actuating at least one first and one second functional unit, wherein the actuating element is movable in a translational and/or rotational motion within a movement range, wherein the first functional unit is actuatable by means of a movement within a first partial region of the movement range and the second functional unit is actuatable by means of a movement within a second partial region of the movement range, wherein a changeover device is provided such that, as a result of a movement of the actuating element through a changeover region between the first and second partial region, an operative connection between the first functional unit and the actuating element can be interrupted and an operative connection can be established between the second functional unit and the actuating element.

An essential aspect of the invention is that, due to the changeover device provided, a movement within the first partial region has no effect on the second functional unit. Conversely, a movement within the second partial region has no effect on the first functional unit. Thus, the user can concentrate on carrying out the first or second function without having to take into account some other function. However, in order to actuate the functional units, only one actuating element is necessary. As a result, the operability of the surgical instrument is improved compared with the prior art.

In the changeover region, or possibly in a sub-region of the changeover region, an operative connection between the actuating element and the first and/or second functional unit can be made or interrupted.

Preferably, at least one arresting device is provided such that the first functional unit, or a partial component thereof, is arrested during a movement of the actuating element within the second partial region, and possibly conversely, such that the second functional unit, or a partial component thereof, is arrested during a movement of the actuating element within the first partial region. The arresting device can be a component part of the changeover device. Arresting of this type also simplifies operation of the surgical instrument. If the first functional unit is, for example, a holding device or grasping device for tissue, it is ensured that the holding device is constant with regard to the force exerted therewith and/or the position thereof.

In a preferred embodiment, the arresting device or the changeover device is a toggle mechanism. The toggle mechanism can be configured such that arresting or changeover can take place when a dead point is passed. In this case, the dead point defines the changeover region. In general, the changeover region can be a point, wherein the changeover can occur when the relevant changeover point is passed. The arresting or changeover with the aid of a toggle mechanism is particularly simple in design and can be carried out in a simple manner.

In another embodiment, the changeover device or the arresting device includes a guide track in which the actuating element can be guided, particularly (substantially) in one movement plane. The guide track can be configured such that changeover or arresting, possibly in cooperation with other components, can be initiated by a movement of the actuating element within the at least one guide track. A guide track of this type simplifies the changeover or arresting and thus the operation of the surgical instrument.

Preferably, the guide track is V-shaped or U-shaped, wherein a first V-limb or U-limb is shorter than a second V-limb or U-limb. Preferably, the guide track is configured such that the arresting is effected when the guide track is arranged within the first, short V-limb or U-limb. In addition, preferably, the guide track can be configured such that the arresting is cancelled when the actuating element is arranged in, or transferred into, the second, longer V-shaped or U-shaped limb. The guide track can possibly be configured such that, on transfer from one limb to the other, the changeover takes place at the same time. Guide tracks of this type are simple in design and simplify operation.

In another embodiment, the guide track is, in particular, an integral component of a housing element, preferably a handle casing. By this means, a component can be omitted, thus reducing costs.

Preferably, the first/second functional unit includes a cutting device, such as, for example, a mechanical cutting device or a laser cutting device, and/or a holding device or grasping device, and/or a coagulation device, in particular a high-frequency coagulation device, and/or a water jet device, particularly a water jet cutting device, and/or an optical apparatus, for example, a camera or an illumination apparatus, and/or a suction device, and/or a washing device, and/or a cryoprobe and/or a biopsy device, such as a biopsy probe or biopsy forceps, and/or preferably a monopolar cutting electrode. More preferably, the first functional unit includes a holding device and the second functional unit includes a cutting device.

Particularly preferably, at least one toothed rack and at least one toothed wheel are provided for transfer of action between the actuating element and at least one functional unit.

Preferably, the toothed wheel can be brought into engagement with a row of teeth which is preferably connected to a housing element, more preferably with a handle casing and, particularly, integrally with the housing element or the handle casing, such that rotation of the toothed wheel brings about a translational displacement of the toothed rack relative to the housing element or the handle casing. This further simplifies the force transfer, such that further components can be omitted, thus reducing costs.

In a further development, the first/second functional unit, particularly the cutting device and/or the holding device is movable by actuating the actuating element, preferably in each position within the corresponding partial region and/or actively in two different directions. This further simplifies operation of the surgical instrument.

In another embodiment, at least one third functional unit, for example, a coagulation device, can be actuated by means of a further (separate) actuating element. By this means, a further function, for example coagulation, can take place independently of the actuation of the first or second functional unit. This simplifies operation.

To facilitate operation, the actuating element can also include a hand trigger.

The actuating element can be rotatable about at least two rotational axes which are spaced apart from one another. Through a change of the rotational axis of this type, various components can have force applied to them particularly easily.

In another embodiment, the actuating element for actuating the first functional unit is rotatable about a first axis, and for actuating the second functional unit, said actuating element is rotatable about a second axis. The changeover can include the displacement of the rotational axes. Actuation of the individual functional units is associated with only a small design effort in this case.

Preferably, a second rotational axis is situated on a central axis of the toggle joint. Alternatively or additionally, a first/second rotational axis can be arranged within the guide track, particularly within the shorter U-limb or V-limb. At least a slight translation can possibly take place during the rotation, so that the rotational axis becomes displaced during the rotation. In this case, the displacement is smaller than 5 mm, and more preferably, smaller than 3 mm. If the actuating element is rotatable about the central axis of the toggle joint, actuation of the corresponding functional unit can be carried out particularly easily.

Preferably, the actuating element is rotatable and a sliding apparatus can be driven translationally, particularly by means of the toggle joint. The sliding apparatus can initiate a particular function, particularly via connecting elements, such as a push rod, and reduces the effort involved in manufacturing.

In another embodiment, a spring element is provided such that a force of the actuating element can be transmitted via the spring element to the first/second functional unit. By means of the interposition of the spring element, the force of the actuating element can be buffered or stored. A spring element of this type can also apply pressure to the first/second functional unit if the first/second functional unit is in an arrested position. For example, if the functional unit is a holding device, the tissue can be held reliably and with a constant force, without requiring the user to take action.

Preferably, at least one spring, preferably a tension spring, is provided such that, on displacement of the functional unit, the spring element exerts a restoring force thereon. A spring element of this type enables the relevant function, for example, the holding of the tissue, to be released or deactivated without active holding by the user.

Preferably, the actuating element is configured such that the movement can be carried out in one plane within the first partial region, and/or the second partial region, and/or the changeover region. This reduces the effort involved during use.

Preferably, the changeover device and/or the arresting device is/are configured reversible such that a reversal of the movement of the actuating element leads to a changeover leading back to the starting condition or to a cancellation of the arresting. This simplifies operation of the instrument.

As a result, the surgical instrument enables ergonomic and effective operation. The (mechanical) decoupling of the partial regions means that no forces are transmitted to the other functional unit or to the actuating element. For example, to grasp tissue, the user must first apply force (generally for actuating the first functional unit). Following arresting, however, the user can work in the second partial region independently of this closing force. The functions can be carried out with the same body parts of the operator (for example, middle finger, and/or ring finger, and/or little finger), while other body parts remain free for operating. For example, the index finger can remain free during operation of a cutting device, so that, similar to the act of firing a pistol, the finger can be used for operating a coagulation switch.

Further advantages result from the use of the invention in a combined coagulation and cutting instrument. Closing a jaw portion of a grasping device and cutting with a cutting device can both take place in the closing direction of the hand trigger. The return of a knife into the starting position, unlocking and opening of the jaw part can be carried out in the contrary direction. This enables a rapid execution of the steps: grasping, coagulating, and cutting. This means that relatively rapid cutting of tissue without coagulation, with only one actuating element, similar to a pair of scissors, is also possible. The toggle mechanism enables withdrawal of the knife, unlocking of the arresting device and the opening of the jaw part in one direction of movement. Coagulation can therefore be carried out repeatedly and relatively reliably, without cutting. The instrument offers a good preparation function, since the jaw part can be actively opened by the user and is not necessarily dependent on a spring.

For coagulation, a separate operating element can be provided, possibly without an associated mechanical functional unit. For coagulation, an electrosurgical generator can be provided which produces a high-frequency current which is passed through the grasped tissue via the instrument. The high-frequency current can be applied in monopolar or bipolar operation. The signal for coagulation is usually given by means of a finger switch, possibly also on the handle, or by a foot switch.

BRIEF DESCRIPTION OF THE DRAWINGS

Example embodiments of the invention are described in greater detail below and illustrated in the drawings, with further advantages and disadvantages explained.

DETAILED DESCRIPTION

In the following description, the same reference signs are used for identical parts and parts acting in a similar manner.

Figure 1:
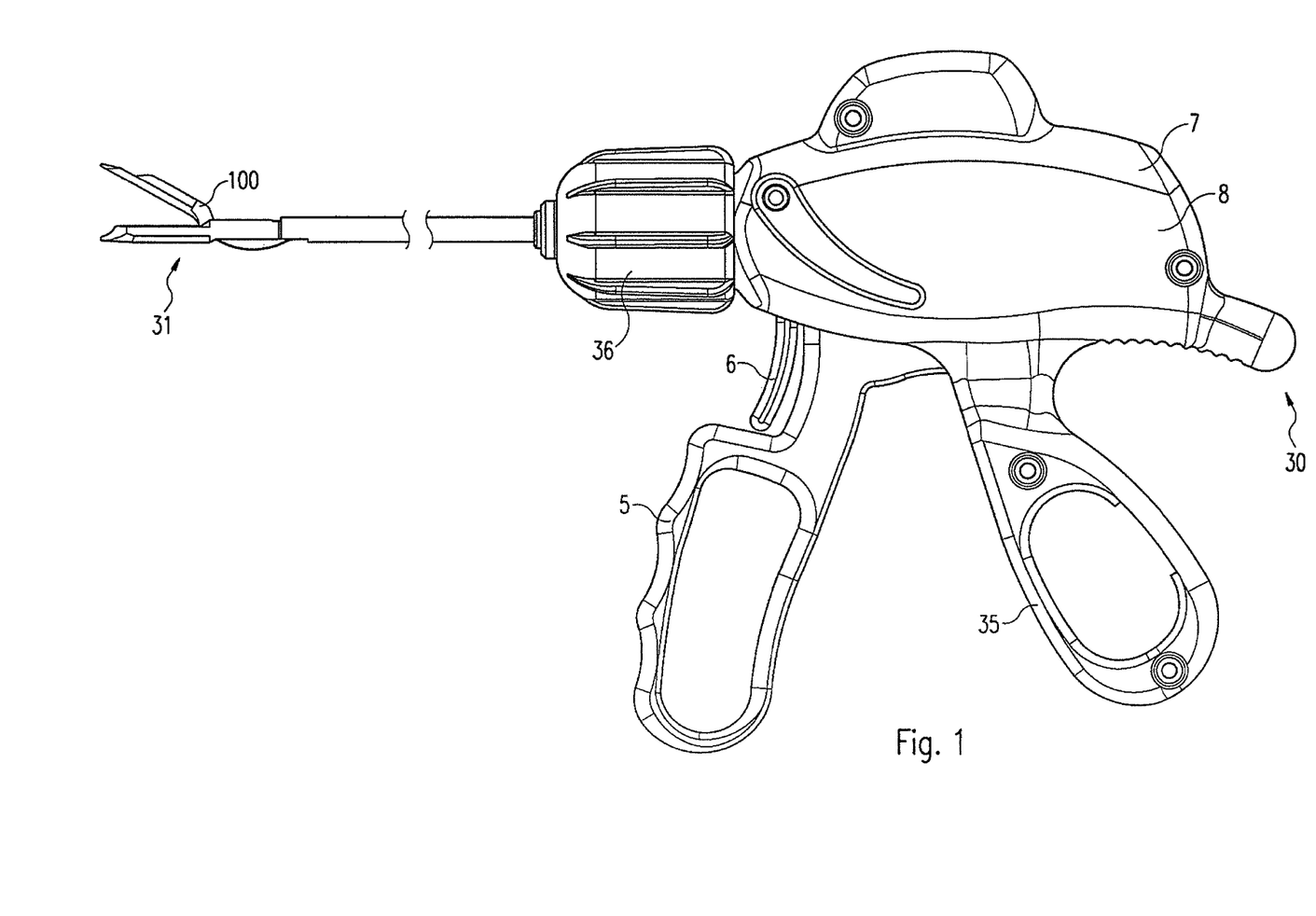
FIG. 1 illustrates an electrosurgical instrument in a side view according to the first embodiment of the invention.

FIG. 1 shows a side view of an electrosurgical instrument which is configured for grasping tissue (first function), for coagulating (third function), and for cutting (second function). The grasping and cutting of tissue is carried out with a common actuating element 5, specifically a hand trigger. The coagulation is controlled via a second actuating element 6, specifically a finger trigger. The hand trigger 5 and the finger trigger 6 are arranged movable relative to a handle housing 7, which includes two mutually opposed handle casings 8.

Figure 2:
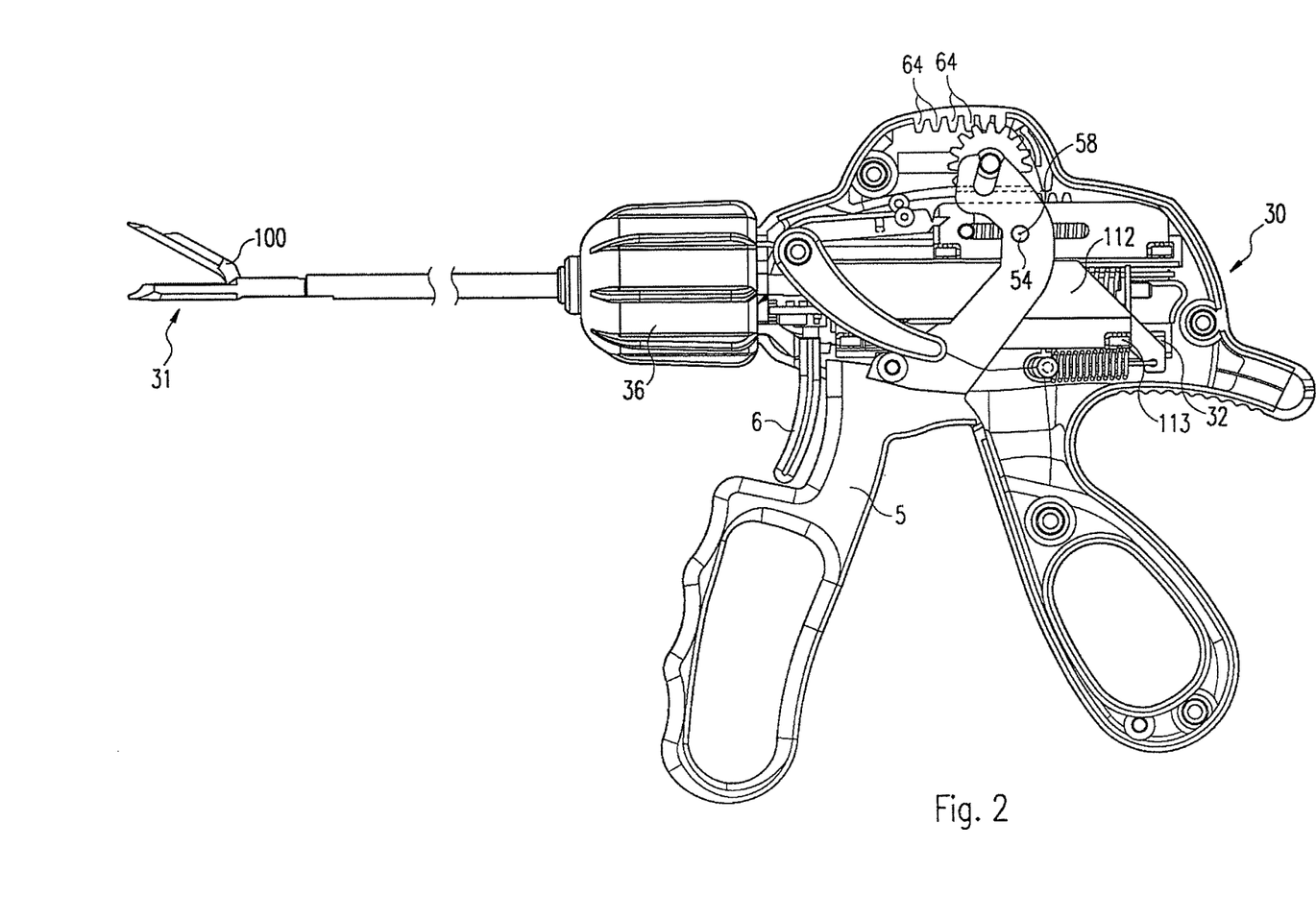
FIG. 2 illustrates the electrosurgical instrument in a first internal view.
Figure 3:
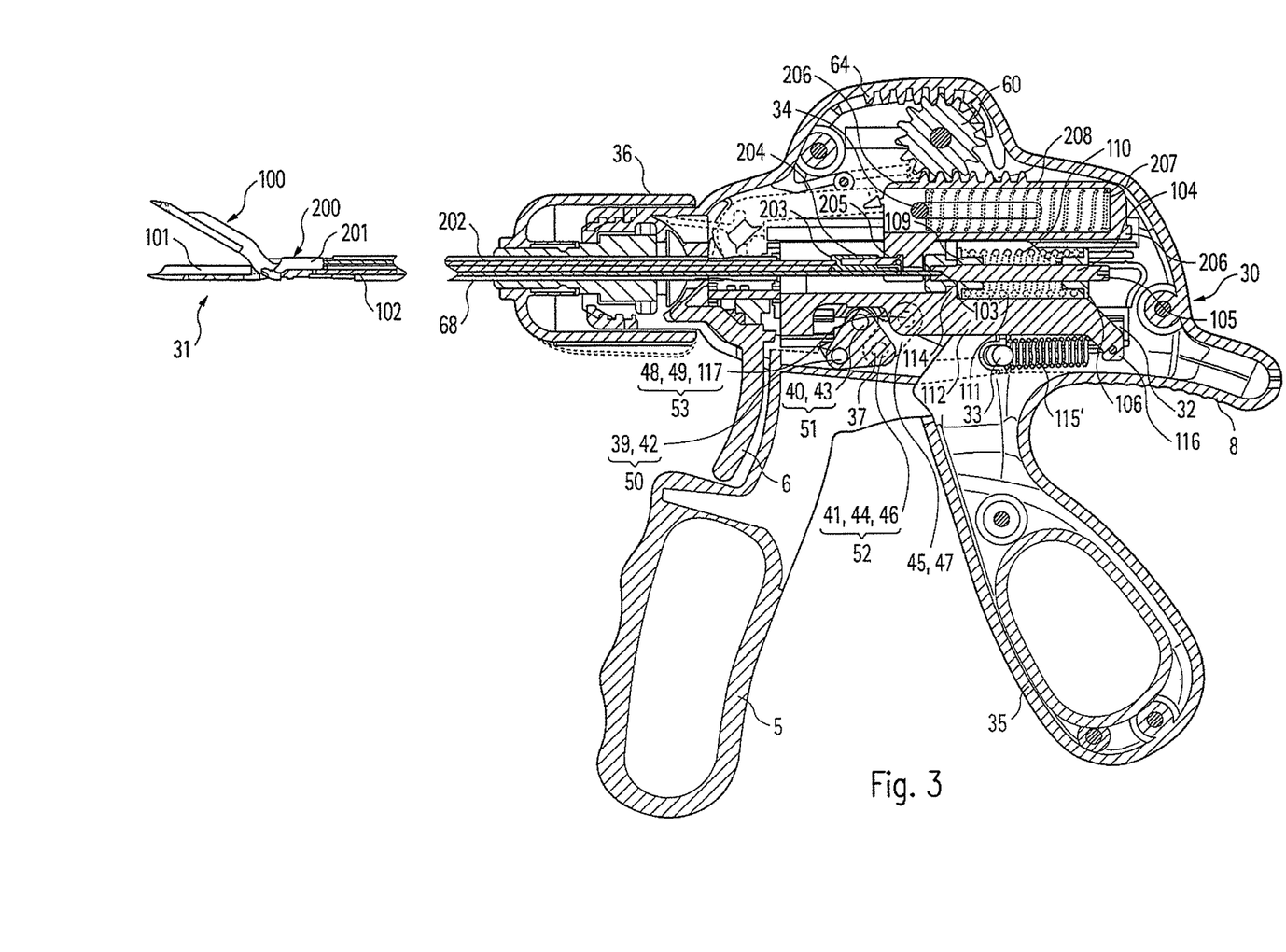
FIG. 3 illustrates the electrosurgical instrument in a first sectional view.

FIGS. 2 and 3 show views of the electrosurgical instrument wherein the hand trigger 5 is arranged in a first position. The hand trigger 5 serves to actuate both a grasping device 100 (as the first functional unit) as well as a cutting device 200 (as the second functional unit).

The grasping device 100 includes a jaw part 101, at which a grasping device rod or a grasping device cable 102 is arranged, so that a pulling movement in the direction of a proximal end 30 results in a closing movement of the jaw part 101 and, conversely, a pushing movement in the direction of a distal end 31 results in opening of the jaw part 101. Here and in the description below, a proximal element/section should be understood as an element/section which lies further removed from the jaw part 101 than a corresponding distal element or a corresponding proximal section.

The grasping device 100 also comprises a draw sleeve 104, which is connected to a proximal end of the grasping device cable 102. The draw sleeve 104 is connected at a proximal end 105 to a spring collar 106 (for example, via a screw thread). At a distal end 107 of the draw sleeve 104, said draw sleeve is guided (in a sliding manner) in a sleeve 108 (threaded sleeve) and subsequently guided proximally adjacent thereto in a second spring collar 109. Arranged between the first spring collar 106 and the second spring collar 109 is a first spring element 110 (specifically a helical spring).

The draw sleeve 104, the first spring collar 106, the second spring collar 109 and the first spring element 110 are also mounted in a recess 111 of a transmission element 112 in sliding manner. The transmission element 112 is mounted within the handle casing 8, specifically within handle casing recesses 32 formed therein, in a sliding manner. Transmission element pegs 113, which are guided in the track-like handle casing recesses 32 (see FIG. 2), serve to mount the transmission element 112 in a sliding manner.

Furthermore, the transmission element 112 has a transmission element stop 114 (and possibly a plurality thereof) which, when the transmission element 112 moves in the proximal direction, exerts a force in the proximal direction on a distal end of the second spring collar 109, which, in turn, exerts a tensional force indirectly via the first spring element 110, the first spring collar 106 and the draw sleeve 104, on the grasping device cable 102 in the proximal direction.

The tensional force acting on the grasping device cable 102 leads to the closing of jaw part 101 until said jaw part is either completely closed or lies against a tissue to be grasped. Variations in tissue thickness can be compensated for particularly easily by the design of the spring element 110 without the tissue being held too loosely or too tightly. The spring element therefore has an energy-saving function, so that operation of the instrument is simplified for the operator with a simple design.

A tension spring 115 (specifically a helical tension spring) is attached, at one end, to the handle casings 8 or to handle casing pins 33 arranged thereon and, at the other end, to a proximal end 116 of the transmission element 112 such that displacement of the transmission element 112 in the proximal direction counteracts a spring force of the tension spring 115. By this means, in the position according to FIGS. 2 and 3, automatic opening of the jaw part 101 can be ensured particularly simply. This simplifies operation of the electrosurgical instrument.

The cutting device 200 includes a knife 201, which is connected to a cutting device rod or a cutting device cable 202. A proximal end 203 of the cutting device cable 202 is connected (via a threaded sleeve 204 and a pin 205) to a transfer element 206. This has the result that a displacement of the transfer element 206 in the distal direction via the cutting device cable 202 leads to a displacement of the knife 201 in the distal direction, so that tissue held in the jaw part 101 can be cut. A second spring element 208 is arranged in a transfer element recess 207, wherein a proximal end of the second spring element 208 contacts a proximal end of the transfer element 206 and a distal end of the second spring element 208 contacts a pin 34, which is immovably connected to (for example, integrally formed onto) the handle casings 8.

The handle casings 8 also form a handle element 35, for example, for accommodating a thumb of the user. A pivot element 36 is also provided, with which the jaw part 101 and/or the knife 201 can be pivoted.

In the position of the electrosurgical instrument according to FIGS. 2 and 3, by means of a closing movement of the hand trigger 5, a force can be transferred, via a toggle mechanism 37, to the transmission element 112, so that said transmission element is displaced in the proximal direction and the jaw part 101 is closed. The toggle mechanism 37 includes a toggle plate 38, which is substantially triangular. The toggle plate 38 includes a first toggle plate bore 39 and a second toggle plate bore 40, as well as toggle plate pins 41 (shown dashed in FIG. 3). A hand trigger pin 42, which is immovably connected to the hand trigger 5, is guided in the first toggle plate bore. A handle casing pin 43, which is immovably connected to the handle casings 8, is guided in the second toggle plate bore 40. The toggle plate pins 41, which project outwardly, are guided in a first transmission plate recess 44 of a first transmission plate 45 and a transmission plate recess 46 of a second transmission plate 47 (shown dotted). The transmission plate recess 44, 46 or the transmission plates 45, 47 lie over one another in the drawings. The transmission plates 45, 47 have second transmission plate recesses 48, 49 (shown dotted in FIG. 3), which are guided by the pins 117, which are immovably connected to the transmission element 112.

As a result, therefore, the toggle mechanism 37 includes a first toggle joint 50, which includes the first toggle plate bore 39 and the hand trigger pin 42, a second toggle joint 51, which includes the second toggle plate bore 40 and the handle casing pin 43, a third toggle joint 52, which includes the toggle plate pins 41 and the transmission plate recesses 44, 46, and a fourth toggle joint 53, which includes the second transmission plate recesses 48, 49 and the pins 117 of the transmission element 112. The toggle joints 50-53 can also be configured differently from the design shown here.

The first toggle joint 50 is immovable relative to the hand trigger 5, the second toggle joint 51 is immovable relative to the handle casings 8, and the fourth toggle joint 53 is immovable relative to the transmission element 112, whereas the third toggle joint 52 is movable relative to the hand trigger 5, the handle casings 8, and the transmission element 112.

Figure 10:
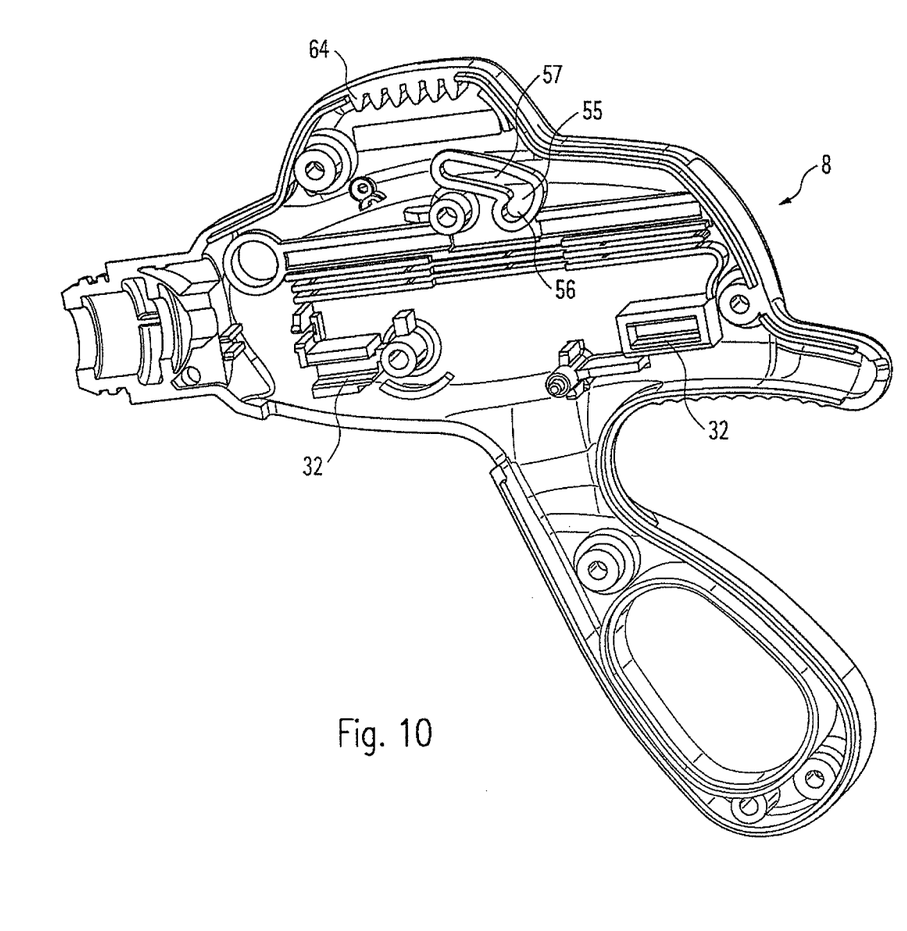
FIG. 10 illustrates a handle casing of the electrosurgical instrument in an internal view.

The hand trigger 5 has one (or more) hand trigger pins 54 (see FIG. 2), held in a V-shaped recess 55 having a shorter V-limb 56 and a longer V-limb 57 (see FIG. 10). In the position according to FIGS. 2 and 3, the hand trigger pin 54 is held in the shorter V-limb 56 and is arrested thereby. A closing movement of the hand trigger 5 thus leads to a rotation of the hand trigger 5 about a first rotational axis 58 (see FIG. 2), which is defined by the hand trigger pin 54. As a result of a rotation about the first rotational axis 58, the transmission plates 45 and 47 are extended relative to the toggle plate 38 (see FIG. 5) until a dead-point position is reached or slightly exceeded (see FIG. 7) and the toggle mechanism 37 is arrested. The dead point is exceeded when the second, third, and fourth joints 51, 52, 53 are arranged in a line. In the position shown in FIGS. 6 and 7, the tension spring 115 is also unable to return the transmission element 112. Reliable and relatively easy adjustable grasping of a tissue (not shown) can therefore be achieved by simple means.

Figure 4:
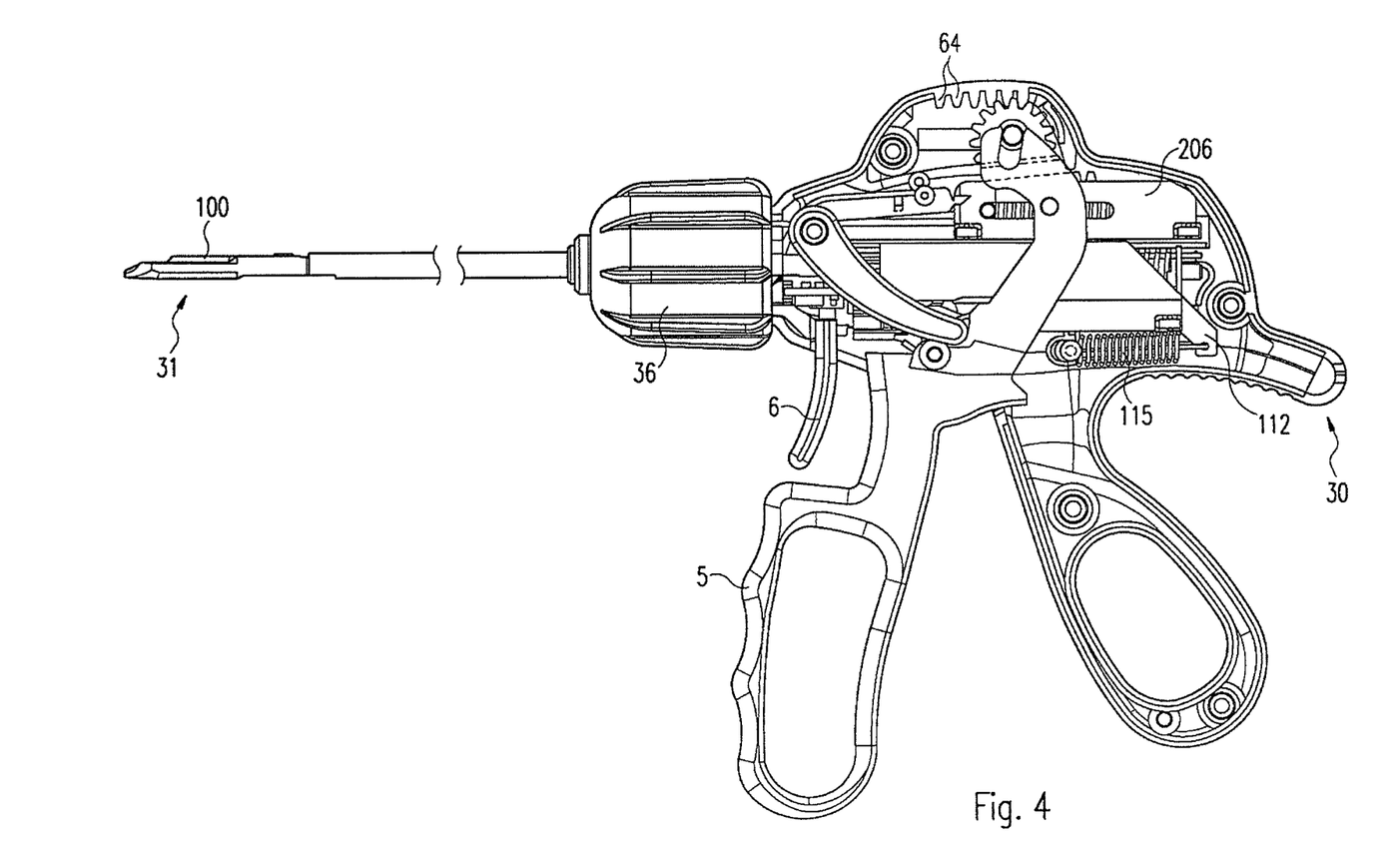
FIG. 4 illustrates the electrosurgical instrument in a second internal view.
Figure 5:
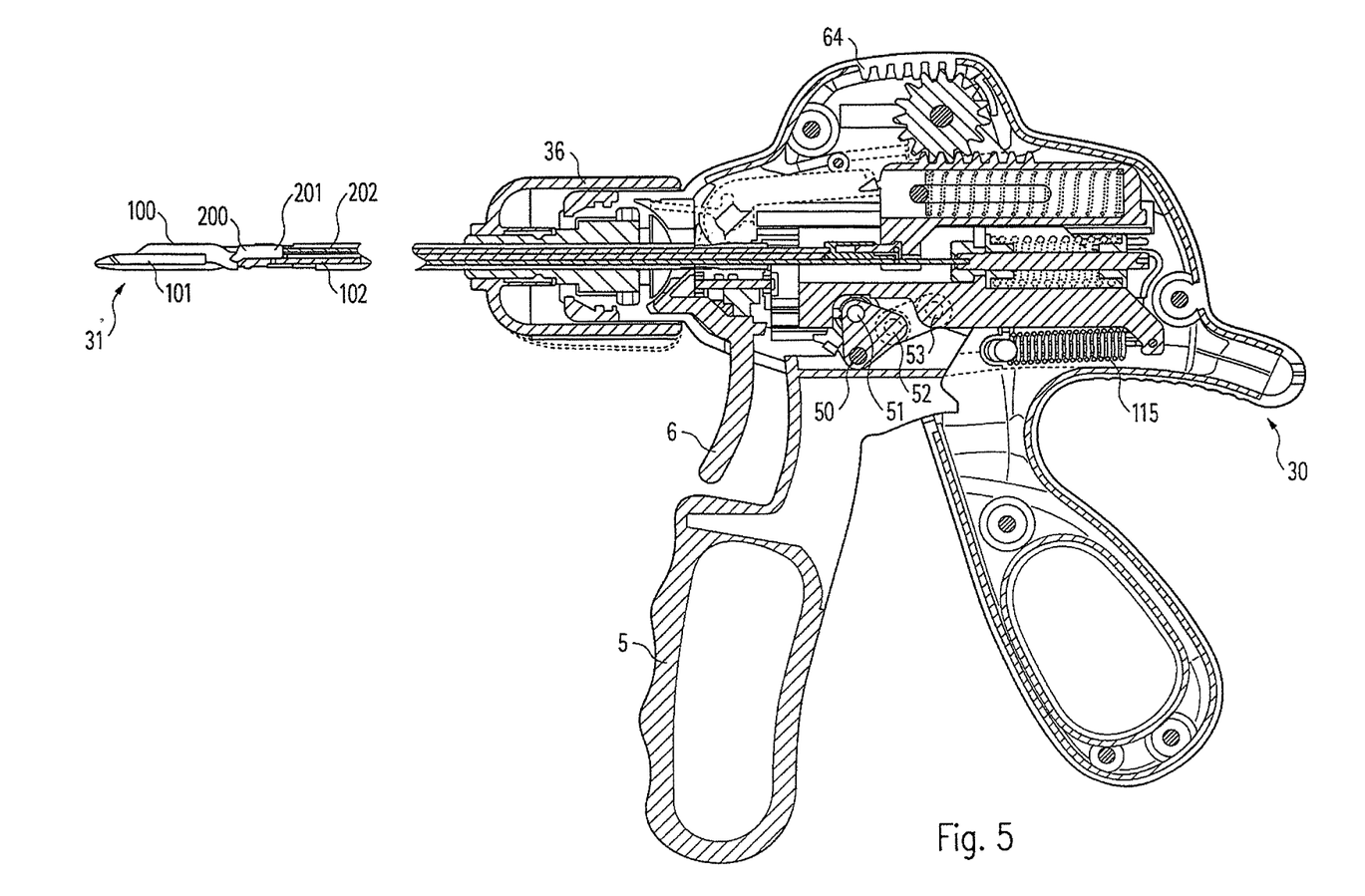
FIG. 5 illustrates the electrosurgical instrument in a second sectional view.
Figure 6:
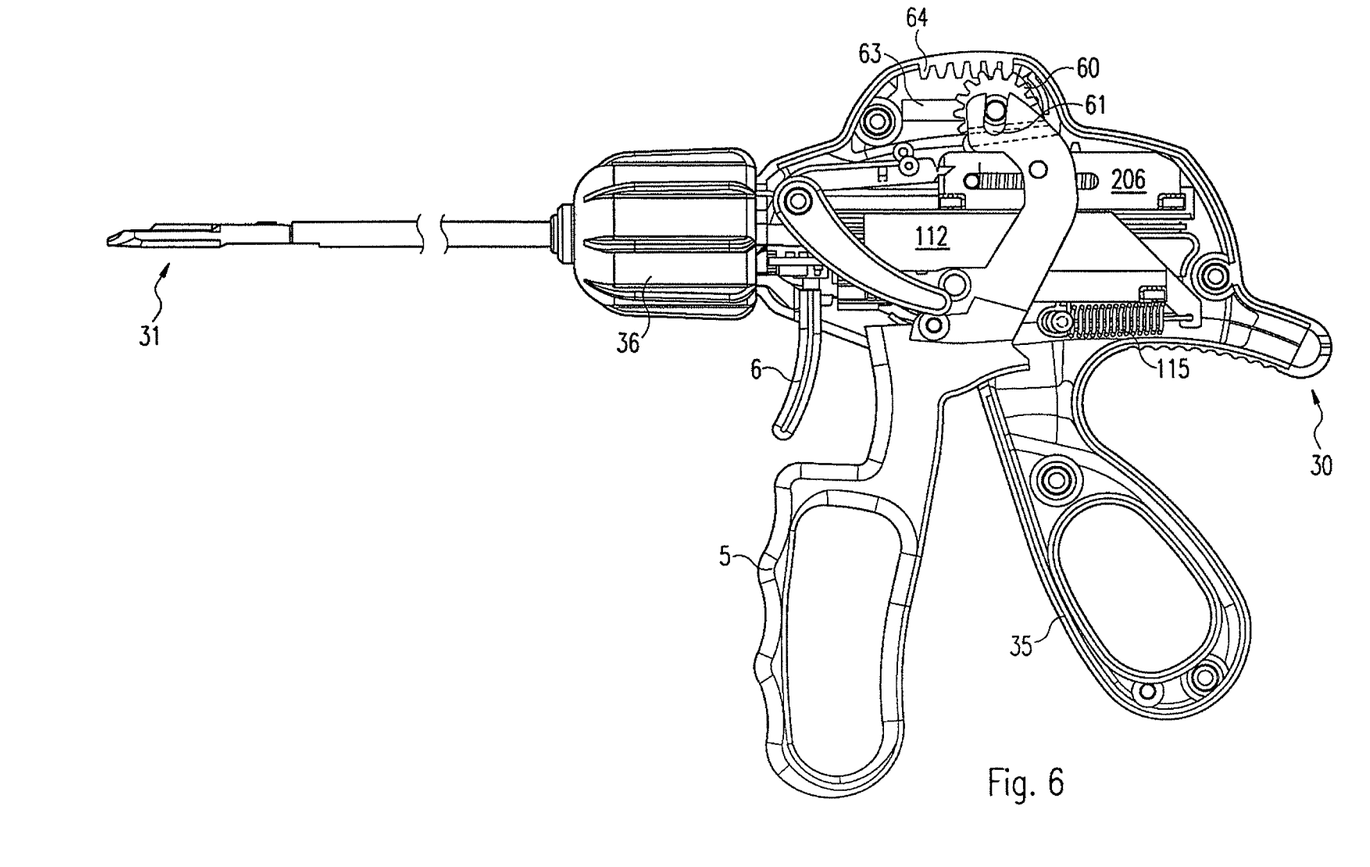
FIG. 6 illustrates the electrosurgical instrument in a third internal view.
Figure 7:
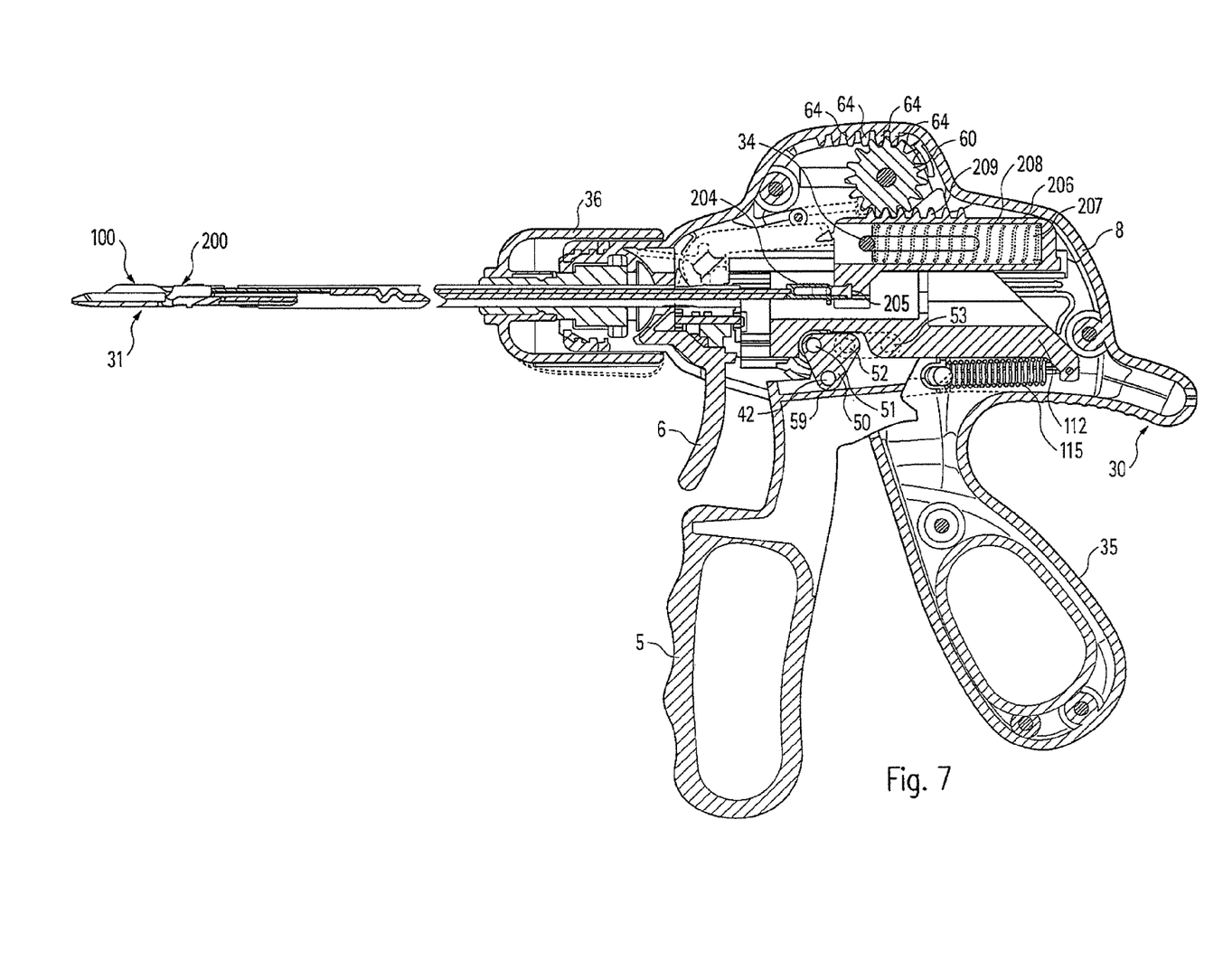
FIG. 7 illustrates the electrosurgical instrument in a third sectional view.

The dead point is reached, for example, when a connecting line between the third and fourth toggle joints 52 and 53 is oriented (approximately) perpendicularly to a connecting line between the first and second toggle joints 50 and 51 (this position is an intermediate position between the position according to FIGS. 4 and 5 and that according to FIGS. 6 and 7).

Figure 8:
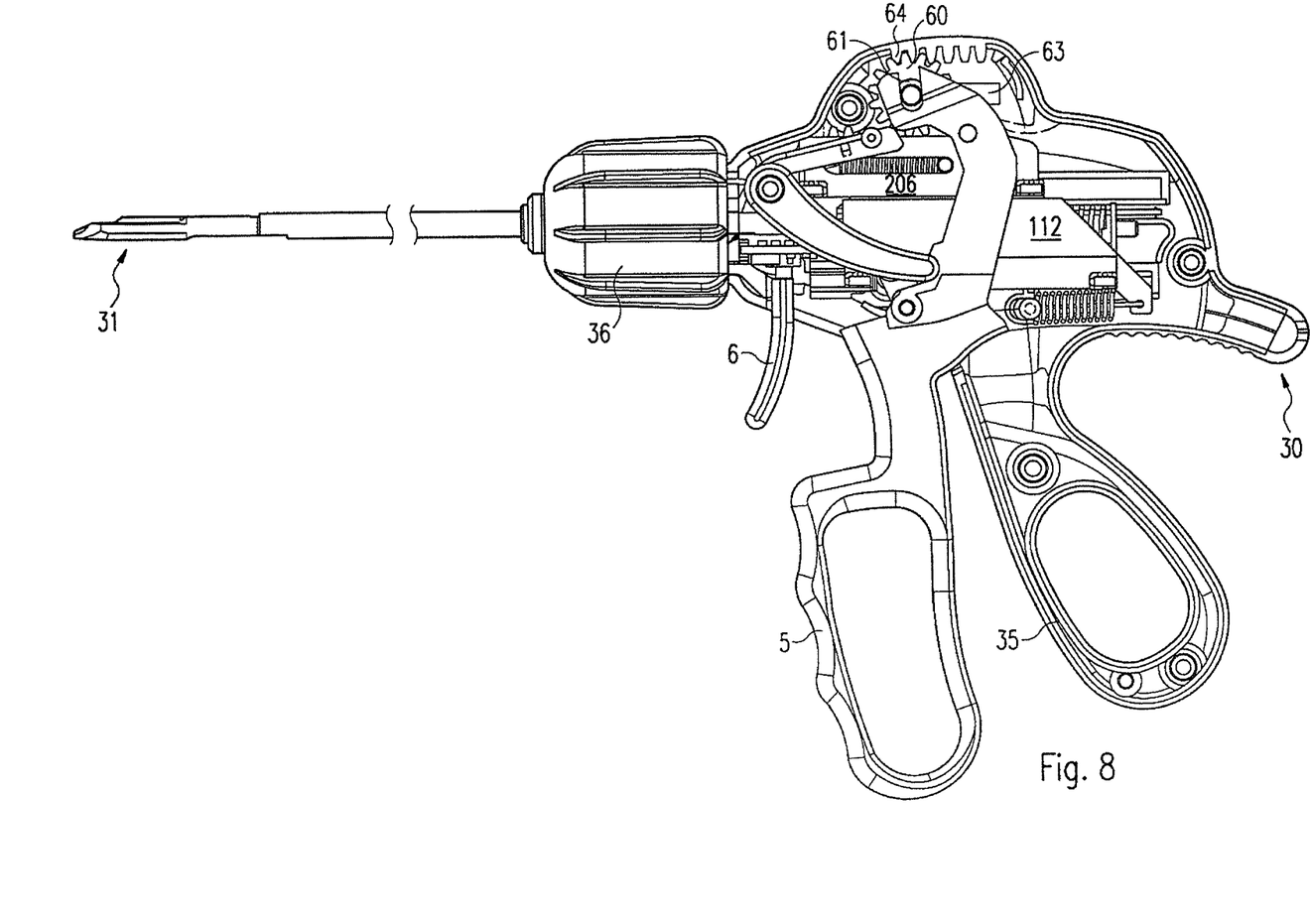
FIG. 8 illustrates the electrosurgical instrument in a fourth internal view.

The V-shaped recess 55 is arranged and configured such that the hand trigger pin 54 is no longer arrested in the position according to FIGS. 7 and 8 (or that the arresting is released). Therefore, in the position according to FIGS. 7 and 8, the hand trigger 5 can rotate about a second rotational axis 59, which is defined by the hand trigger pin 42. Further closing of the hand trigger 5 then leads to a rotation of the hand trigger 5 about the second rotational axis 59, so that a toothed wheel 60, which is mounted within a (radially extending, elongated) hand trigger recess 61, can slide (in the distal direction) along an elongated handle casing recess 63 (wherein a corresponding handle casing recess 63 can be provided at one or both of the handle casings 8). In the process, the hand trigger pin 54 slides in the (slightly curved) V-limb 57 of the V-shaped recess 55. In order to compensate for the slightly curved path of the V-shaped recess, the hand trigger recess 61 is configured elongated so that the toothed wheel 60 can be displaced in the radial direction within the hand trigger recess 61.

Figure 9:
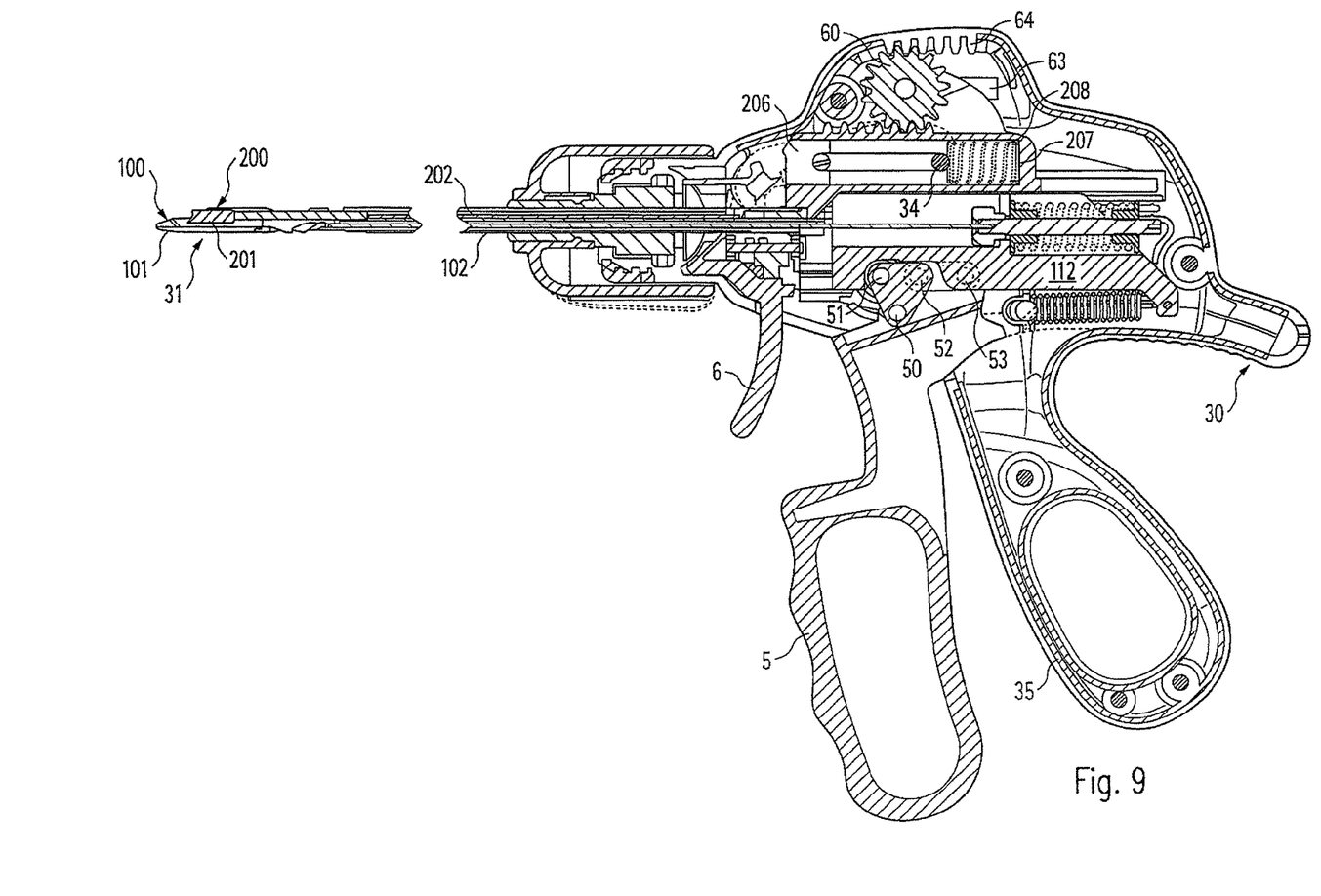
FIG. 9 illustrates the electrosurgical instrument in a fourth sectional view.

Starting from the position according to FIGS. 6 and 7, the toothed wheel 60 is therefore displaced in the distal direction within the elongated handle casing recess 63 as far as an end position according to FIGS. 8 and 9. The provision of handle casing teeth 64 causes the toothed wheel 60 to rotate due to the displacement and can also displace the transfer element 206, which has transfer element teeth 209, in the distal direction. As a result, the knife 201 is displaced in the distal direction by means of the cutting device cable 202, to part the tissue. The arrangement of the toothed wheel 60 between the handle casing teeth 64 and the transfer element teeth 209 enables the transfer element 206 to be displaced, by means of a relatively small displacement of the toothed wheel 60 or a relatively small rotation of the hand trigger 5 about the second rotational axis 59, by a relatively large distance. This simplifies operation of the electrosurgical instrument.

The position as shown in FIGS. 6 and 7, in the first place, and as shown in FIGS. 8 and 9, in the second place, defines at least one section of a second partial region of a movement range of the hand trigger 5, in which only the cutting device 200 is actuated. Within a first partial region of the movement range defined, at least partially by the positions according to FIGS. 2 and 3, in the first place, and FIGS. 4 and 5, in the second place, the grasping device 100 alone can be operated. The positions of the surgical instrument according to FIGS. 4 and 5, in the first place, and FIGS. 6 and 7, in the second place, define a changeover region, within which arresting of the grasping device 100 is achieved when the hand trigger 5 is closed and arresting of the cutting device 200 is released.

A third functional unit, specifically a coagulation functional unit, can be operated by means of the second actuating element (the finger trigger) 6 separately from the hand trigger 5.

The gasping device 100 can be moved back and forth at will in the first partial region of the movement range and the cutting device 200 can be moved back and forth at will in the second partial region of the movement range, thus further improving operability. Particularly when cutting tissue, it is advantageous if the knife 201 can be moved back and forth for parting, resulting in a relatively smooth cutting edge. It is also ensured during gasping of tissue that, in each position, the jaw part 101 can be further opened or further closed. Alternatively, it is also conceivable (in deviation from the embodiment shown) to provide further locking means which also permit arresting within the first or second partial region, so that at particular discrete positions, only movement in one direction is possible.

Two jaw halves of the jaw part 101 serve for grasping and coagulating tissue. In the first partial region, the jaw part halves can be opened and closed. When the hand trigger 5 is pulled, for example, by means of a closing movement of the hand of the user, the jaw part 101 is closed by means of the grasping device 100. Tissue can thus be grasped and coagulated. The coagulation does not necessarily require a mechanical functional unit.

If the hand trigger 5 is pulled beyond a particular point, the grasping device 100 locks and the jaw part 101 remains in the closed state. According to the described embodiment, the toggle mechanism 37 serves to provide the locking. If the hand trigger 5 is in the second partial region, driving the cutting device 200, said hand trigger 5 is (decoupled) from the first partial region and from the grasping device 100. If the hand trigger 5 is pulled farther in the second partial region, the cutting device 200 moves the knife 201 in the distal direction through the firmly held tissue and parts said tissue. If the hand trigger 5 is moved back again in the direction of the locking point, the knife 201 is withdrawn again. If the hand trigger 5 is moved beyond the locking point, the locking is released and the jaw part halves can be opened.

In general, the first functional unit is preferably actuatable by extending the toggle joint and the second functional unit by a rotation about the second rotational axis. Thus a transition from a pulling movement to a pushing movement is achieved by simple means during the changeover, wherein the user does not need to perform a direction change during actuation with the actuating element, thus simplifying operation of the instrument.

The grasping device cable 102 and/or the cutting device cable 202 are preferably guided in a tubular shaft 68.

It should be noted that all the parts described above are example embodiments of the invention, particularly the details shown in the drawings. Variations thereof are the usual practice of persons skilled in the art.

The invention claimed is:

1. A surgical instrument, particularly an electrosurgical instrument, comprising:
   an actuating element for actuating at least one first functional unit and one second functional unit; and
   a changeover device, wherein the actuating element is movable in a translational and/or rotational motion within a movement range having a first partial region and a second partial region, wherein:
   the first functional unit is actuatable by a movement within the first partial region,
   the second functional unit is actuatable by a movement within the second partial region,
   a changeover region is located between the first partial region and the second partial region, and
   a movement of the actuating element through the changeover region can interrupt an operative connection between the first functional unit and the actuating element and an operative connection can be established between the second functional unit and the actuating element.

2. The surgical instrument according to claim 1, further comprising at least one arresting device, wherein the first functional unit and the second functional unit comprise partial components; and
   wherein at least one partial component of the first functional unit is arrested during a movement of the actuating element within the second partial region, particularly in a pre-tensioned position, and at least one partial component of the second functional unit is arrested during a movement of the actuating element within the first partial region.

3. The surgical instrument according to claim 2, wherein the changeover device comprises a toggle mechanism.

4. The surgical instrument according to claim 2, wherein the arresting device comprises a toggle mechanism.

5. The surgical instrument according to claim 3, wherein:
   the changeover device comprises at least one guide track in which the actuating element can be guided in one movement plane,
   the guide track is V-shaped or U-shaped having a first V/U-limb and a second V/U-limb,
   the first V/U-limb is shorter than the second V/U-limb, and
   the guide track is an integral component of a handle housing or a handle casing.

6. The surgical instrument according to claim 4, wherein:
   the arresting device comprises at least one guide track in which the actuating element can be guided in one movement plane,
   the guide track is V-shaped or U-shaped having a first V/U-limb and a second V/U-limb,
   the first V/U-limb is shorter than the second V/U-limb, and
   the guide track is an integral component of a handle housing or a handle casing.

7. The surgical instrument according to claim 5, wherein the first functional unit and the second functional unit are movable by actuating the actuating element in a position in the first partial region, the second partial region, or actively in two different directions.

8. The surgical instrument according to claim 7, wherein the first functional unit or the second functional unit comprises a cutting device, a grasping device, a holding device, a coagulation device, a water jet device, an optical apparatus, a suction device, a washing device, a cryoprobe, a biopsy device, or a cutting electrode.

9. The surgical instrument according to claim 8, wherein the coagulation device is a high-frequency coagulation device.

10. The surgical instrument according to claim 8, wherein the water jet device is a water jet cutting device.

11. The surgical instrument according to claim 8, wherein the optical apparatus is a camera or an illumination system.

12. The surgical instrument according to claim 8, wherein the biopsy device is a biopsy probe or biopsy forceps.

13. The surgical instrument according to claim 8, wherein the cutting electrode is monopolar and extensible.

14. A surgical instrument, particularly an electrosurgical instrument, comprising:
   an actuating element for actuating at least one first functional unit and one second functional unit;
   a changeover device; and
   at least one toothed rack and at least one toothed wheel for transmission of a force applied by the actuating element to at least one functional unit, wherein:
   the actuating element is movable in a translational and/or rotational motion within a movement range having a first partial region and a second partial region, the first functional unit is actuatable by a movement within the first partial region, the second functional unit is actuatable by a movement within the second partial region, a changeover region is located between the first partial region and the second partial region, a movement of the actuating element through the changeover region can interrupt an operative connection between the first functional unit and the actuating element and an operative connection can be established between the second functional unit and the actuating element, and the toothed wheel can be brought into engagement with a row of teeth which is immovably connected to a handle housing such that rotation of the toothed wheel brings about a translational displacement of the toothed rack relative to the handle housing.

15. The surgical instrument according to claim 14, wherein the handle housing comprises a handle casing.

16. The surgical instrument according to claim 14, further comprising:

at least one third functional unit; and a further actuating element, wherein the third functional unit is actuated by a further actuating element.

17. The surgical instrument according to claim 16, wherein the third functional unit comprises a coagulation device.

18. The surgical instrument according to claim 16, wherein the further actuating element comprises a finger trigger.

19. The surgical instrument according to claim 16, wherein the actuating element comprises a hand trigger.

20. The surgical instrument according to claim 16, wherein:

the actuating element is rotatable about at least two rotational axes, a first rotational axis and a second rotational axis being spaced apart from one another, the actuating element for actuating the first functional unit is rotatable about a first axis, the actuating element for actuating the second functional unit, is rotatable about a second axis, and the changeover device comprises a toggle mechanism having a central axis.

21. The surgical instrument according to claim 20, wherein the first and second rotational axes are positioned on a central axis of the toggle mechanism.

22. A surgical instrument, particularly an electrosurgical instrument, comprising:

an actuating element for actuating at least one first functional unit and one second functional unit;

a changeover device;

at least one toothed rack and at least one toothed wheel for transmission of a force applied by the actuating element to at least one functional unit; and at least one first spring element such that a force of the actuating element is transmitted via the spring element to a functional unit, wherein the actuating element is movable in a translational and/or rotational motion within a movement range having a first partial region and a second partial region;

wherein the first functional unit is actuatable by a movement within the first partial region;

wherein the second functional unit is actuatable by a movement within the second partial region;

wherein a changeover region is located between the first partial region and the second partial region;

wherein a movement of the actuating element through the changeover region can interrupt an operative connection between the first functional unit and the actuating element and an operative connection can be established between the second functional unit and the actuating element; and wherein the toothed wheel can be brought into engagement with a row of teeth which is immovably connected to a handle housing such that rotation of the toothed wheel brings about a translational displacement of the toothed rack relative to the handle housing.

23. The surgical instrument according to claim 22, further comprising:

a sliding apparatus;

the changeover device comprises a toggle mechanism; and the actuating element is rotatable and with the toggle mechanism can drive a sliding apparatus translationally.

24. The surgical instrument according to claim 23, wherein the actuating element is configured such that the movement can be carried out within the first partial region and/or the second partial region and/or the changeover region in one plane.

25. The surgical instrument according to claim 24, wherein the changeover device is configured reversible such that a reversal of the movement leads to a changeover leading back to the starting condition or to a cancellation of the arresting.

* * * * *

UNITED STATES PATENT AND TRADEMARK OFFICE
CERTIFICATE OF CORRECTION

PATENT NO. : 8,936,595 B2  
APPLICATION NO. : 13/078625  
DATED : January 20, 2015  
INVENTOR(S) : Lothar Mitzlaff et al.

Page 1 of 1

It is certified that error appears in the above-identified patent and that said Letters Patent is hereby corrected as shown below:

On the title page, Item (73), Assignee, please add -- ERBE Elektromedizin Gmbh, Tubingen, Germany --

Signed and Sealed this
Twenty-third Day of February, 2016

Michelle K. Lee
*Director of the United States Patent and Trademark Office*